United States Patent
Yamaguchi et al.

[11] Patent Number: 5,945,211
[45] Date of Patent: Aug. 31, 1999

[54] COMPOSITE MATERIAL CARRYING ZINC OXIDE FINE PARTICLES ADHERED THERETO AND METHOD FOR PREPARING SAME

[75] Inventors: Yasuhide Yamaguchi; Masahiko Nakano; Kenji Suzuoka, all of Saitama, Japan

[73] Assignee: Mitsui Mining and Smelting Co., Ltd., Tokyo, Japan

[21] Appl. No.: 08/797,625

[22] Filed: Feb. 7, 1997

[30] Foreign Application Priority Data

| Feb. 22, 1996 | [JP] | Japan | 8-035118 |
| May 9, 1996 | [JP] | Japan | 8-114863 |
| May 9, 1996 | [JP] | Japan | 8-114864 |
| May 9, 1996 | [JP] | Japan | 8-114865 |
| Nov. 1, 1996 | [JP] | Japan | 8-291719 |

[51] Int. Cl.$^6$ ..................................... B32B 3/26
[52] U.S. Cl. .......................... 428/325; 428/389; 427/180
[58] Field of Search ..................... 428/325, 365, 428/389; 427/180

[56] References Cited

U.S. PATENT DOCUMENTS

| 4,199,322 | 4/1980 | Danna et al. | 8/186 |
| 5,668,076 | 9/1997 | Yamagushi | 502/243 |

FOREIGN PATENT DOCUMENTS

| 0 379 581 | 8/1990 | European Pat. Off. . |
| 1 292 309 | 4/1969 | Germany . |
| 4-164813 | 6/1992 | Japan . |
| 4-164814 | 6/1992 | Japan . |
| 5-117910 | 5/1993 | Japan . |
| 5-156510 | 6/1993 | Japan . |
| 1 707 113 | 1/1992 | U.S.S.R. . |

*Primary Examiner*—Timothy M. Speer
*Attorney, Agent, or Firm*—Young & Thompson

[57] ABSTRACT

A zinc oxide fine particle-adhered composite material consists essentially of a substrate and zinc oxide fine particles adhered thereto. The composite material is characterized in that the zinc oxide fine particles deposited, from an aqueous medium, on the surface of the substrate are firmly adhered to the surface without using any binder and the zinc oxide fine particles are substantially exposed on the surface. The composite material is prepared by, for instance, a method which comprises the step of coming an aqueous suspension of zinc oxide fine particle in contact with a substrate to thus deposit the zinc oxide fine particles on the surface of the substrate. The composite material allows for the zinc oxide particles to sufficiently show their antibacterial, deodorizing, UV absorbing, photocatalytic, stain-proofing and purifying activities without any delay.

20 Claims, No Drawings

COMPOSITE MATERIAL CARRYING ZINC OXIDE FINE PARTICLES ADHERED THERETO AND METHOD FOR PREPARING SAME

BACKGROUND OF THE INVENTION (A) Field of the Invention

The present invention relates to a composite material which carries zinc oxide particles, adhered thereto, (hereinafter referred to as "zinc oxide particle-adhered composite material") which shows various activities such as antibacterial, deodorizing, UV absorbing, photocatalytic, stain-proofing and purifying activities and a method for preparing the composite material. More specifically, the present invention relates to a zinc oxide particle-adhered composite material wherein zinc oxide particles are firmly adhered to the surface of a substrate without using any binder and exposed on the surface and exhibit antibacterial, deodorizing, UV absorbing, photocatalytic, stain-proofing and purifying activities as well as a method for preparing the composite material.

(B) Description of the Prior Art

It has been known that zinc oxide shows an antibacterial activity; such a deodorizing activity that it can selectively absorb sulfur-containing gases such as hydrogen sulfide and sulfur dioxide gas; a UV absorbing activity; a photocatalytic activity like titanium oxide; and stain-proofing and purifying activities. It has been reported that a photocatalytic substance such as zinc oxide shows its photocatalytic activity when light rays including ultraviolet rays irradiate the catalyst and the oxidation activity thereof is induced by the photocatalytic activity (generally referred to as "photocatalytic reaction") to thus decompose gases which give out a bad smell and to show its antibacterial activity.

Zinc oxide particles have often been fixed to a substrate for making the most use of the foregoing activities such as antibacterial, deodorizing, UV absorbing, photocatalytic, stain-proofing and/or purifying activities. As methods for fixing zinc oxide particles to the substrate, there have conventionally been proposed and used, for instance, a method which comprises kneading zinc oxide fine particles into a resin as a molding material to thus incorporate the particles into resin molded articles or fibers; or a method which comprises dispersing zinc oxide fine particles in paint and varnish to give dispersed zinc oxide particle-containing paint and varnish and applying the paint and varnish to a desired substrate, or applying a dispersion comprising zinc oxide particles and a binder to a substrate and then subjecting the coated substrate to a heat-treatment to thus firmly adhere the particles to the substrate (see, for instance, JP-A-5-156510).

If kneading zinc oxide particles into a resin or dispersing them in paint and varnish as described above, most of the zinc oxide particles are enclosed or embedded in resins or paint and varnish and are hardly exposed on the surface thereof. For this reason, the strong antibacterial and deodorizing activities of zinc oxide fine particles are not effectively used and when such paint and varnish is applied onto fibrous products, the fibrous products lose their flexibility and the paint and varnish cannot easily be applied uniformly to the products. As a means for eliminating this problem, there has been proposed a method which comprises kneading zinc oxide particles into a resin and then etching the surface of the resulting resin by, for instance, irradiation thereof with an ion beam or ozone to thus expose, on the surface, zinc oxide particles as much as possible (see, for instance, JP-A-1-156576). However, this method does not permit a substantial increase in the number of zinc oxide particles exposed on the surface and a new problem arises, i.e., such an etching treatment would rather make the resin or fibers brittle.

In case where a dispersion is applied onto a substrate (the method disclosed in JP-A-5-156510), the coated layer must be subjected to a heat-treatment in order to evaporate the dispersion medium and to ensure the adhesion of particles to the substrate by the use of a binder. Moreover, the activity of zinc oxide particles per se and the effects which may be expected by the incorporation of zinc oxide particles would be deteriorated or impaired because of the adhesion of the binder onto the surface of the particles. Accordingly, the antibacterial effect thereof is low and almost equivalent to that observed when they are kneaded into resins. Further the resins and binders would be deteriorated due to the choking effect of zinc oxide.

Also known is a method which comprises the steps of covering a substrate with zinc hydroxide and then decomposing, with heating, the layer of zinc hydroxide to give a coating layer of zinc oxide, but in this case, the substrate should be heated to a high temperature on the order of not less than 150° C. and this may, in turn, be accompanied by deformation, change of properties or melting of the substrate depending on the material of the substrate. Moreover, the coated film has a tendency to be easily peeled off during heating and accordingly, it is difficult to obtain a body carrying zinc oxide firmly adhered thereto.

The thermal spraying technique may be used as the method for adhering zinc oxide particles to the surface of a substrate, but the particle size of the zinc oxide particles formed by this method is not less than several micrometers ($\mu$m) and these particles are welded together. Therefore, if molten zinc oxide particles are adhered to, for instance, a fibrous substance as the substrate, the substrate loses its softness and the touch and is not practically acceptable. Zinc oxide may likewise be adhered to a substrate by the sputtering and vapor deposition techniques, but these techniques simply permit the coating of the outermost layer of a substrate and cannot uniformly cover the entire surface of, for instance, fibrous products (including the surface of internal fibers thereof) with zinc oxide particles.

Organic and inorganic chemicals other than zinc oxide have been used as antibacterial and/or deodorizing agents and some organic drugs have sometimes been applied to the surface of a substrate. However, zinc oxide is desirably used as a material which has not only safety and durability, but also antibacterial and deodorizing activities.

In addition, JP-A-4-164813 discloses a method for preparing zinc oxide fine particles comprising the steps of dropwise adding an aqueous alkaline solution to an aqueous solution of a zinc salt at a temperature of not less than 60° C. and precipitating zinc oxide particles at a final pH of not less than 9 and JP-A-4-164814 discloses a method for preparing zinc oxide fine particles comprising the steps of dropwise adding an aqueous solution of a zinc salt to an aqueous alkaline solution at a temperature of not less than 60° C. and precipitating zinc oxide particles at a final pH of not less than 9, but these patents do not disclose a zinc oxide fine particle-adhered composite material wherein the zinc oxide fine particles are firmly bonded to the surface of a substrate without using any binder and are sufficiently exposed on the surface as well as a method for preparing the composite material.

BRIEF SUMMARY OF THE INVENTION

The present invention has been developed in order to solve the foregoing various problems associated with the conventional techniques and accordingly, an object of the present invention is to provide a zinc oxide fine particle-adhered composite material which does not suffer from the foregoing drawbacks as well as a method for preparing the same and more specifically to provide a zinc oxide fine particle-adhered composite material in which the zinc oxide fine particles are firmly adhered to the surface of a substrate without using any binder and are sufficiently exposed on the surface of the substrate and in which the zinc oxide fine particles can satisfactorily show their activities such as antibacterial, deodorizing, UV absorbing, photocatalytic, stain-proofing and purifying activities as well as a method for preparing such a composite material.

The inventors of this invention have conducted various studies to accomplish the foregoing objects, have unexpectedly found out that zinc oxide fine particles are firmly adhered to the surface of a substrate without using any binder by depositing zinc oxide fine particles on the substrate surface while substrate with an aqueous suspension of zinc oxide fine particles, or contacting a substrate carrying a zinc ion-containing acidic solution attached thereto with an aqueous alkaline solution to thus cause a reaction therebetween under alkaline conditions and have thus completed the present invention on the basis of this finding.

More specifically, the zinc oxide fine particle-adhered composite material according to the present invention consists essentially of a substrate and zinc oxide fine particles adhered thereto, exhibits antibacterial, deodorizing, UV absorbing, photocatalytic, stain-proofing and purifying activities and is characterized in that the zinc oxide fine particles deposited, from an aqueous medium, on the surface of the substrate are firmly adhered to the surface without using any binder and that the particles are substantially exposed on the surface of the substrate.

Preferably, the zinc oxide fine particle-adhered composite material according to the present invention consists essentially of zinc oxide fine particles which are deposited on the substrate surface from an aqueous suspension of zinc oxide fine particles and have an average particle size of not more than 0.5 $\mu$m, or which are deposited on the substrate surface by contacting the substrate carrying a zinc ion-containing acidic solution attached thereto with an aqueous alkaline solution to thus cause a reaction therebetween under alkaline conditions and have an average particle size of not more than 0.1 $\mu$m.

According to a first methodological aspect of the present invention, there is provided a method for preparing a zinc oxide fine particle-adhered composite material consisting essentially of a substrate and zinc oxide fine particles adhered thereto, which comprises the step of depositing the zinc oxide fine particles on the surface of the substrate while contacting the substrate with an aqueous suspension of zinc oxide fine particles, the zinc oxide fine particle-adhered composite material exhibiting antibacterial, deodorizing, UV absorbing, photocatalytic, stain-proofing and purifying activities and the zinc oxide fine particles being firmly adhered to the surface of the substrate without using any binder and being substantially exposed on the surface.

According to a second methodological aspect of the present invention, there is provided a method for preparing a zinc oxide fine particle-adhered composite material consisting essentially of a substrate and zinc oxide fine particles adhered thereto, which comprises the step of contacting the substrate carrying a zinc ion-containing acidic solution adhered thereto with an alkaline aqueous solution to thus cause a reaction therebetween under alkaline conditions, the zinc oxide fine particle-adhered composite material exhibiting antibacterial, deodorizing, UV absorbing, photocatalytic, stain-proofing and purifying activities and the zinc oxide fine particles having an average particle size of not more than 0.1 $\mu$m, being firmly adhered to the surface of the substrate without using any binder and being substantially exposed on the surface thereof.

According to a third methodological aspect of the present invention, there is provided a method for preparing a zinc oxide fine particle-adhered composite material consisting essentially of a substrate and zinc oxide fine particles adhered thereto, which comprises the steps of contacting the substrate carrying a zinc ion-containing acidic solution adhered thereto with an alkaline aqueous solution to thus cause a reaction therebetween under alkaline conditions and, immediately thereafter, ripening the substrate carrying the zinc oxide fine particles deposited thereon in a solution which hardly solubilizes zinc oxide for not less than 5 minutes, the zinc oxide fine particle-adhered composite material exhibiting antibacterial, deodorizing, UV absorbing, photocatalytic, stain-proofing and purifying activities and the zinc oxide fine particles having an average particle size of not more than 0.1 $\mu$m, being firmly adhered to the surface of the substrate without using any binder and being substantially exposed on the surface.

In the second and third methodological aspect of the present invention, the reaction under alkaline conditions and the ripening steps are preferably carried out at a temperature of not less than 50° C.

DETAILED DESCRIPTION

The composite material and the method for preparing the same according to the present invention will hereinafter be described in more detail.

The zinc oxide fine particle-adhered composite material of the present invention consists essentially of a substrate and zinc oxide fine particles deposited on and adhered to the surface of the substrate as has been discussed above. The substrate on which the zinc oxide fine particles are deposited may be any materials such as synthetic fibers, natural fibers, inorganic fibers, fibrous products obtained therefrom, paper products, molded articles of synthetic resins and ceramics and may have any shape. Preferred are fibers, fibrous products such as woven and nonwoven fabrics, paper products and films. In case the substrate is a fibrous or paper product, individual fibers constituting these products are considered to be substrates in the present invention and accordingly, zinc oxide fine particles are adhered to the surface of these individual fibers.

It has conventionally been believed that the use of a binder is an essential requirement for adhering inorganic powder such as titanium oxide to the surface of resins such as polypropylene and polyethylene because of low surface activity of these resins and accordingly, binders have been used for such purposes. However, it has unexpectedly been confirmed that zinc oxide fine particles are firmly adhered to the surface of a substrate without using any binder if the zinc oxide fine particles are deposited on the substrate surface by contacting the substrate with an aqueous suspension of zinc oxide fine particles or if a substrate carrying the zinc ion-containing acidic solution attached thereto is brought into contact with the aqueous alkaline solution to thus cause a reaction therebetween under alkaline conditions. In particular, zinc oxide fine particles can uniformly be deposited on thermoplastic fibers and therefore, each individual fiber constituting a woven or nonwoven fabric as a substrate may easily and uniformly be covered with zinc oxide fine particles.

In the zinc oxide fine particle-adhered composite material of the present invention, the zinc oxide fine particles deposited, from aqueous medium, on the foregoing substrate surface by the method discussed above are firmly bonded to the surface without using a binder and are sufficiently exposed thereon and the composite material accordingly shows the desired effects such as antibacterial, deodorizing, UV absorbing, photocatalytic, stain-proofing and purifying effects.

The term "firmly adhered to" herein used means that zinc oxide fine particles are adhered to the surface to such an extent that the fine particles are not dropped off or separated from the composite material even when the latter is subjected to washing and/or drying operations. Moreover, the term "deposited, from an aqueous medium, on the substrate surface" is herein used to exclude direct formation of zinc oxide on the substrate surface by, for instance, anodization of zinc and zinc oxide layer formed by depositing zinc oxide, from gaseous phase, on the substrate surface by, for instance, thermal spraying of zinc oxide and sputtering and vapor deposition techniques.

Moreover, the term "antibacterial" herein used means that bacteria such as *Escherichia coli* and mold are killed. The term "deodorizing" herein used means that the composite material can reduce the amount of gases which give out a bad smell and means for the reduction is not restricted to any specific one. Specific examples thereof are decomposition, adsorption or chemical reactions. Zinc oxide is reactive with, in particular, sulfur atom-containing gases and is effective for eliminating or reducing factory exhaust gases and bad smells emitted from lavatory and crude waste such as hydrogen sulfide, sulfur dioxide gas and methylmercaptan. The term "UV absorbing" means that the composite material absorbs ultraviolet rays and cuts off UV light rays, the term "photocatalytic" means that zinc oxide is excited by the irradiation with light rays such as ultraviolet rays to thus generate electrons and positive holes and the electrons thus generated are transferred from zinc oxide to the substance adhered to the surface thereof to thus decompose the substance through oxidation or reduction. The term "stain-proofing" herein means that zinc oxide decomposes contaminants adhered to the surface thereof to thus reduce the extent of the surface stain and the term "purifying" herein used means that zinc oxide decomposes contaminants present in a gas or a liquid to thus hold the gas or liquid in a clean condition.

The present invention permits a zinc oxide fine particle-adhered composite material having any desired shape by adhering zinc oxide fine particles to a woven or nonwoven fabric or a paper product as a substrate and then forming the product into an article having a desired shape; or forming a woven or nonwoven fabric or a paper product as a substrate into an article having a desired shape and then adhering zinc oxide fine particles to the appropriately shaped article.

If the zinc oxide fine particle-adhered composite material is an antibacterial filter having gas permeability and water permeability, a gas permeable and water permeable zinc oxide fine particle-adhered filter having a desired shape and antibacterial, deodorizing and stain proofing functions can be prepared, for instance, by adhering zinc oxide fine particles to a woven or nonwoven fabric as a substrate and then forming the fabric into a desired pleated filter shape; or forming a woven or nonwoven fabric as a substrate into a desired pleated filter shape and then adhering zinc oxide fine particles to the filter-shaped article.

Zinc oxide shows antibacterial and deodorizing effects, can absorb moisture, is applied to the buttocks of babies as zinc white (baby powder) to prevent diaper rash and accordingly, zinc oxide has been known to be quite safe to human bodies and hardly causes allergic reactions. Accordingly, there can be provided various articles in the form of zinc oxide fine particle-adhered composite materials, more specifically, a table napkin, a hand towel, a towel, a wet tissue, a diaper, a liner, a napkin, a mask and sanitary goods showing various functions such as antibacterial, deodorizing and stain proofing functions as well as gas permeability, water permeability and water retention characteristics, by firmly adhering zinc oxide fine particles to the surface of substrates for sanitary use according to the method of this invention without using any binder.

The substrates for use in making sanitary goods may be any material such as fibrous products (for instance, woven and nonwoven fabrics) of synthetic and natural fibers and paper products and may have any shape, which are appropriately selected depending on each particular use of the sanitary good. Preferred substrates for use in making sanitary goods are fibrous products such as woven and nonwoven fabrics and paper products. In particular, when using a nonwoven fabric as a substrate and depositing zinc oxide on the nonwoven fabric, effective antibacterial and deodorizing functions may be imparted to the resulting composite material while using a small amount of the zinc oxide absorbed thereon.

Zinc oxide fine particles may be adhered to the surface of substrates for sanitary goods prior to forming the substrate (such as woven or nonwoven fabric) into a desired shape of the sanitary good or after forming the substrate into a desired shape.

As has been discussed above in detail, zinc oxide shows antibacterial and antifungal activities, can absorb moisture, and zinc oxide has been known to be quite safe to human bodies and hardly causes allergic reactions. Therefore, there can be provided a useful antibacterial and antifungal fibrous sheet as an embodiment of the zinc oxide fine particle-adhered composite material if firmly adhering zinc oxide fine particles to the surface of a fibrous sheet-like substrate such as a woven or nonwoven fabric used in the home and human living environment according to the present invention without using any binder. Examples of such antibacterial and antifungal fibrous sheet include backings for carpets and rug, a backing for wallpaper, a mat, a carpet, underlay sheets for bedclothes and household furnishings, covers for sleeping mats, covers for pillows and packaging materials. The use of these antibacterial and antifungal sheets would permit the control of breedings of bacteria, mold and ticks.

Such fibrous substrates to which zinc oxide fine particles are adhered may be any material such as fibrous products (for instance, woven and nonwoven fabrics) of synthetic and natural fibers and may have any shape, which can appropriately be selected depending on each particular use of the fibrous sheet. Preferred fibrous substrates are fibrous products such as woven and nonwoven fabrics. In particular, when using a nonwoven fabric as a substrate and depositing zinc oxide on the surface of the nonwoven fabric, effective antibacterial and antifungal functions may be imparted to the resulting composite material while using a reduced amount of the zinc oxide absorbed thereon.

Zinc oxide fine particles may be adhered to the surface of the fibrous sheet-like substrates for use in making antibacterial and antifungal fibrous sheets prior to forming the substrate (such as woven or nonwoven fabric) into a desired fibrous sheet-like shape or after forming the substrate into a desired fibrous sheet-like shape.

In addition, there can be provided a UV light screening film by adhering zinc oxide fine particles to a transparent film.

All of the zinc oxide fine particles are completely exposed in the zinc oxide fine particle-adhered composite material according to the present invention. Therefore, the desired antibacterial, deodorizing, UV absorbing, photocatalytic, stain proofing and purifying effects can be ensured even when a quite small amount of zinc oxide fine particles are adhered to the substrate as compared with that required when the particles are kneaded into a substrate or a mixture of zinc oxide fine particles and a binder is applied. In particular, the difference, in deodorizing quality, of these products is quite conspicuous. This is because, the dissolution of a trace amount of zinc ions gives rise to the antibacterial activity, while the deodorizing effect is in proportion to the surface area of zinc oxide.

In the first embodiment of the method according to the present invention, an aqueous suspension of zinc oxide fine particles is brought into contact with a substrate to thus deposit the zinc oxide fine particles on the surface of the substrate. The aqueous suspension of zinc oxide fine particles is prepared by suspending zinc oxide fine particles in water. The water may be tap water, distilled water or de-ionized water, but it is preferred to prepare the zinc oxide fine particle-adhered composite material using water free of mineral ions depending on the applications of the composite material. Moreover, if the zinc oxide concentration in the aqueous suspension of zinc oxide fine particles is too high, the suspension is liable to cause agglomeration and to cause non-uniform deposition of zinc oxide fine particles. Therefore, the concentration is preferably not more than 5% by weight and more preferably not more than 1% by weight. Regarding the pH value of the aqueous suspension of zinc oxide fine particles, it preferably ranges from neutral to weak alkaline region, more preferably about 7 to 9, from the viewpoint of the amount of the zinc oxide fine particles adhered to the substrate. Moreover, the formation of the composite material is not greatly influenced by the temperature of the suspension.

In the first embodiment of the method of the present invention, the aqueous suspension of zinc oxide fine particles can be brought into contact with the substrate by, for instance, immersing the substrate in the aqueous suspension, or spraying the substrate with the aqueous suspension or applying the aqueous suspension onto the substrate. After contacting the substrate with the aqueous suspension, the substrate is washed with water and then dried. The contact time required till the substrate is washed with water is affected by the concentration of the zinc oxide present in the aqueous suspension, but such a contact time of about 1 to 2 seconds is sufficient for ensuring sufficient adhesion of the zinc oxide fine particles to the substrate surface. Therefore, the contact time is in general not more than one minute and preferably not more than 30 seconds.

To prevent any dropping off of the zinc oxide fine particles from the substrate during using the zinc oxide fine particle-adhered composite material, i.e., to prevent the presence of zinc oxide fine particles which may drop off during using the composite material, it is preferred to sufficiently remove excess zinc oxide fine particles by injecting a water jet or washing with crumpling, after contacting the substrate with the aqueous suspension. Although the drying temperature and time are sometimes restricted by the kinds of substrates, they are generally those required for sufficiently evaporating wash water. In addition they vary depending on the drying means such as hot air drying or high temperature drying without application of any air stream. For instance, a substrate such as a nonwoven fabric can be hot air-dried at 100° C. for a time on the order of several seconds to several minutes.

The zinc oxide fine particles can firmly be adhered to the surface of a substrate without using any binder by simply depositing the particles, from an aqueous suspension of zinc oxide fine particles, on the substrate surface according to the first embodiment of the method of the present invention. The reason of this has not yet clearly been elucidated, but it would be assumed that the zinc oxide fine particles in the aqueous suspension come in contact with the substrate while the fine particles are partially dissolved, active points are accordingly generated on the surface of the fine particles due to such dissolution and thus the fine particles are firmly adhered to the substrate surface; or that the dissolved zinc oxide serves as a binder after drying the substrate carrying zinc oxide particles deposited thereon to thus firmly adhere the particles to the substrate surface.

If the substrate used in the foregoing production method has a hydrophobic surface, the surface is first treated with, for instance, a surfactant, an acid, an alkali, an alcohol, ozone, ultraviolet rays and radiant rays to thus convert the surface into a hydrophilic one and then zinc oxide fine particles are deposited on the surface of the substrate thus treated and consequently, a greater amount of zinc oxide fine particles can firmly adhered to the substrate surface.

The zinc ion-containing acidic solution used in the second and third embodiments of the method of the present invention is prepared by, for instance, dissolving a water-soluble zinc salt such as zinc sulfate, zinc chloride or zinc nitrate in water, and the alkaline solution used therein is one prepared by dissolving an alkali such as sodium hydroxide, potassium hydroxide or lithium hydroxide in water. The water used in these embodiments may be the same as those described above in connection with the foregoing first embodiment.

In the second and third embodiments of the method of the present invention, it is an essential requirement that the zinc ion-containing acidic solution is brought into contact with the alkaline aqueous solution to thus react them under alkaline conditions while maintaining the contact state between the substrate and the zinc ions. A temperature of not less than room temperature may be used as the temperature when contacting the zinc ion-containing acidic solution with the alkaline aqueous solution without any problem, but the reaction is preferably carried out at a temperature of not less than 50° C. in order to adhere a larger amount of zinc oxide to the substrate surface within a shorter period of time. If the reaction temperature is less than room temperature, it would become difficult to obtain zinc oxide having a low impurity content. Moreover, the reaction velocity is apt to be reduced and it would become difficult to sufficiently deposit and adhere zinc oxide fine particles having an average particle size of 0.1 $\mu$m to the surface of the substrate.

If the surface of the substrate is hydrophobic, the surface is first treated with, for instance, a surfactant, an acid, an alkali, an alcohol, ozone, ultraviolet rays and radiant rays to thus convert the surface into a hydrophilic one and then zinc oxide fine particles are deposited on and adhered to the surface of the substrate thus treated and consequently, a greater amount of zinc oxide fine particles can firmly be adhered to the substrate surface.

In the third embodiment of the production method of the present invention, the substrate carrying a zinc ion-containing acidic solution adhered to the surface thereof, as has been described above, is brought into contact with an alkaline aqueous solution to thus cause a reaction under alkaline conditions and immediately thereafter, the substrate is ripened by immersing it in a solution which hardly solubilizes zinc oxide for not less than 5 minutes. Preferably, the substrate carrying a zinc ion-containing acid solution adhered to the surface thereof, as has been described above, is brought into contact with an alkaline aqueous solution at a temperature of not less than 50° C. to thus cause a reaction therebetween under alkaline conditions and immediately thereafter, the substrate is ripened by immersing it in a solution which hardly solubilizes zinc oxide and is maintained at a temperature of not less than 50° C. for not less than 5 minutes.

The term "a solution which hardly solubilizes zinc oxide" herein used means that solubility of zinc oxide in the solution is much smaller than solubility of zinc oxide in water. Such a solution includes a solution saturated or nearly saturated with zinc ion, concretely, aqueous zinc sulfate solution, aqueous zinc chloride solution, aqueous zinc nitrate solution, aqueous zinc acetate solution.

If the pH value of the solution which hardly solubilizes zinc oxide is not less than 9, zinc oxide having very low impurity content is adhered to the substrate surface. For this reason, the pal value of the solution is more preferably not less than 9. The ripening temperature and time are not restricted to specific ranges insofar as they can ensure sufficient deposition and adhesion of zinc oxide fine particles having an average particle size of 0.1 $\mu$m to the substrate surface and it is sufficient to ripen at a temperature of not less than room temperature for not less than 5 minutes. If the reaction temperature is lower than room temperature, it would become difficult to obtain zinc oxide fine particles having a low impurity content. Moreover, the reaction velocity is apt to be reduced and it would become difficult to sufficiently deposit and adhere zinc oxide fine particles having an average particle size of 0.1 $\mu$m to the surface of the substrate.

There can be produced a zinc oxide fine particle-adhered composite material consisting essentially of a substrate and zinc oxide fine particles which have an average particle size of not less than 0.1 $\mu$m, are adhered to the substrate surface without using any binder and are exposed on the surface if the method of the present invention is carried out under the foregoing conditions.

In the zinc oxide fine particle-adhered composite material according to the present invention, the zinc oxide fine particles are adhered to the surface of the substrate in the absence of a binder and sufficiently exposed on the surface. Therefore, the composite material allows for the zinc oxide particles to sufficiently show their antibacterial, deodorizing, UV absorbing, photocatalytic, stain-proofing and purifying activities without any delay.

The present invention will hereinafter be described in more detail with reference to the following non-limitative working Examples and Comparative Examples.

EXAMPLE 1

To one liter each of de-ionized water, there was added 1 g, 2 g or 5 g of zinc oxide powder (primary particle size of about 0.2 $\mu$m) produced according to the dry method, followed by sufficient stirring to give a suspension. The pH value of these suspensions were found to be 7.6. A polypropylene nonwoven fabric (prepared by the spunbonding method; basis weight: 20 g/m$^2$; fiber diameter: about 20 $\mu$m; size: 10 cm×10 cm) was immersed in each suspension maintained at room temperature, followed by stirring for 30 seconds. After completion of the stirring, the nonwoven fabrics were sufficiently washed with distilled water and then dried at 100° C. for 5 minutes.

The concentration of each zinc oxide suspension and the rate of weight gain of each nonwoven fabric were determined and they are summarized in the following Table:

| concentration of Zinc Oxide Suspension | Rate of Weight Gain of Nonwoven Fabric |
|---|---|
| 0.1% by weight | 3.4% by weight |
| 0.2% by weight | 3.7% by weight |
| 0.5% by weight | 3.6% by weight |

Moreover, each nonwoven fabric thus treated was examined by the X-ray diffraction analysis and as a result, it was confirmed that all of the nonwoven fabrics after the treatment showed the peaks to be ascribed to zinc oxide. Moreover, the fibrous surface of the nonwoven fabric was observed using a scanning electron microscope (SEM) and as a result, it was also confirmed that each zinc oxide fine particle was firmly adhered to each fibrous surface of the nonwoven fabric. Furthermore, a drop of an indicator: Xylenol Orange was added to each nonwoven fabric. As a result, it was confirmed that the indicators dropped on all of the nonwoven fabrics immediately caused a color change from an orange color to a deep pink color. This clearly indicates that zinc ions are released from the fabrics and in turn indicates that the zinc oxide particles are exposed on the substrate surface and immediately react with the indicator.

The same procedures used above were repeated except for using tap water in place of de-ionized water and it was confirmed that the same results were obtained.

COMPARATIVE EXAMPLE 1

To one liter of de-ionized water free of zinc oxide powder, maintained at room temperature, there was added the same nonwoven fabric used in Example 1, followed by stirring the same time used in Example 1 and drying under the same conditions used in Example 1. The surface of the nonwoven fabric after the treatment was visually observed and it was found to be smooth and there was not observed any deposit. A drop of an indicator: Xylenol Orange was dropwise added to the nonwoven fabric, but the orange color of the indicator did not cause any change over a long time period.

COMPARATIVE EXAMPLE 2

There were admixed 20% by weight of zinc oxide powder identical to that used in Example 1, 30% by weight of an acrylic resin binder and 50% by weight of ethyl acetate to give paint and varnish, followed by application of the paint and varnish to a nonwoven fabric (10 cm×10 cm) identical to the polypropylene nonwoven fabric used in Example 1 and drying at 60° C. for a half day.

A drop of an indicator: Xylenol Orange was added to the nonwoven fabric. As a result, it was found that the indicator dropped on the nonwoven fabric caused a slight color change from an orange color to a pale pink color after about 3 minutes. More specifically, the time required till the indicator caused such a color change was very long as compared with the nonwoven fabric obtained in Example 1. This clearly indicates that zinc oxide was only slightly exposed on the surface of the nonwoven fabric.

EXAMPLE 2

The nonwoven fabric obtained in Example 1 in which the zinc oxide aqueous suspension concentration had been 0.5% by weight and the nonwoven fabrics prepared in Comparative Examples 1 and 2 were placed in each separate glass laboratory dish and 150 µl each of a culture medium of *Escherichia coli* (including about $3 \times 10^4$ *E. coli* cells) was dropwise added to these laboratory dishes. The culture medium was recovered from each nonwoven fabric immediately after the dropwise addition and after a predetermined time from the dropwise addition, followed by dropping each culture medium thus recovered on a standard agar medium, cultivation thereof for 24 hours and counting the number of colonies formed. The results thus obtained are summarized in the following Table 1.

TABLE 1

| Contact Time with Bacterial Culture Medium | Number of Colonies After Cultivation | | |
|---|---|---|---|
| | Example 1 | Comparative Example 1 | Comparative Example 2 |
| 0 hour | $8.3 \times 10^3$ | $9.8 \times 10^3$ | $8.8 \times 10^3$ |
| 1 hour | $2.0 \times 10^2$ | $9.9 \times 10^3$ | $8.9 \times 10^3$ |
| 2 hours | $1.3 \times 10^2$ | $9.8 \times 10^3$ | $5.3 \times 10^3$ |
| 3 hours | $\leq$D.L. | $8.1 \times 10^3$ | $2.7 \times 10^3$ |

D.L.: Detection Limit

As seen from these data listed in Table 1, the nonwoven fabric of Example 1 which carried zinc oxide adhered to the surface thereof exhibited an excellent antibacterial activity, but the nonwoven fabric of Comparative Example 1 which had not been treated with zinc oxide could not kill *E. coli* cells adhered thereto. In addition, the nonwoven fabric of Comparative Example 2 in which zinc oxide particles had been adhered to the fabric using a binder was found to be inferior to the nonwoven fabric of Example 1 in the rapid antibacterial action.

EXAMPLE 3

The nonwoven fabric obtained in Example 1 in which the zinc oxide aqueous suspension concentration had been 0.5% by weight and the nonwoven fabric prepared in Comparative Example 1 each was exposed to solar rays or light rays from a black light for 2 weeks. Each nonwoven fabric was cut into pieces of 2×8 cm, followed by putting two pieces in layers, fixing both ends thereof and determination of tensile strength according to the method for testing nonwoven fabric having general fiber length (JIS L1906).

The results thus obtained are listed in the following Table 2.

TABLE 2

| Kind of Nonwoven Fabric | Exposure Time (week) | Tensile Strength (kgf) | |
|---|---|---|---|
| | | Solar Rays | Light Rays from Black Light |
| Example 1 | 0 | 3.30 | 3.30 |
| Example 1 | 2 | 3.47 | 3.39 |
| Comp. Ex. 1 | 0 | 4.20 | 4.20 |
| Comp. Ex. 1 | 2 | 3.32 | 4.00 |

The data listed in Table 2 clearly indicate that the nonwoven fabric of Example 1 to which the zinc oxide had been adhered did not cause any deterioration of the nonwoven fabric even when exposed to solar rays or light rays from a black light. Moreover, the zinc oxide-adhered nonwoven fabric was brought into contact with a silk cloth or a black cotton cloth and the fabric was visually inspected for the removal of the zinc oxide from the nonwoven fabric according to the method defined in JIS K5400, but there was not observed any removal of the zinc oxide particles from the fabric.

EXAMPLE 4

To one liter of de-ionized water, there was added 3 g of zinc oxide powder (primary particle size of about 20 nm) produced according to the wet synthesis method, followed by sufficient stirring to give a suspension. The pH value of the suspension was found to be 7.8. A polyethylene nonwoven fabric (prepared by the spunbonding method; size: 10×10 cm) was immersed in the suspension maintained at room temperature, followed by stirring for 30 seconds. After completion of the stirring, the nonwoven fabrics were sufficiently washed with distilled water and then dried at 100° C. for 5 minutes.

The weight gain of the nonwoven fabric was found to be 3.2% by weight. Moreover, the nonwoven fabric thus treated was examined by the X-ray diffraction analysis and it was proved that the nonwoven fabric showed the peaks ascribed to zinc oxide. Moreover, the fibrous surface of the nonwoven fabric was observed using a scanning electron microscope (SEM) and as a result, it was also proved that the zinc oxide fine particles were firmly adhered to the fibrous surface of the nonwoven fabric. Furthermore, a drop of an indicator: Xylenol Orange was added to the nonwoven fabric. As a result, it was proved that the indicator dropped on the nonwoven fabric immediately caused a color change from an orange color to a deep pink color. This clearly indicates that zinc ions are released from the fabric.

The nonwoven fabric was placed in a 9 1 volume sealable glass container and methyl mercaptan was injected into the container at a concentration of 40 ppm, but the concentration thereof was rapidly reduced with time. More specifically, the concentration was reduced to 8 ppm after 30 minutes from the injection and to not more than 1 ppm after 120 minutes from the injection. This clearly indicates that the nonwoven fabric treated with zinc oxide shows very high deodorizing activity.

EXAMPLE 5

A polypropylene nonwoven fabric (prepared by the spunbonding method; basis weight: 20 g/m$^2$; fiber diameter: about 20 μm; size: 10 cm×10 cm) was immersed in a surfactant solution (0.5% by weight aqueous sodium oleate solution) for 15 minutes, followed by washing with distilled water and then drying at 100° C. for 5 minutes. Separately, a nonwoven fabric was provided, which was identical to that used above except that it was not treated with a surfactant. On the other hand, zinc oxide powder (primary particle size: about 50 nm) prepared by the wet synthesis method was dispersed in one liter each of de-ionized water in various amounts, followed by sufficient stirring to give each corresponding aqueous suspension. The foregoing nonwoven fabrics were immersed in these aqueous suspensions maintained at room temperature, followed by stirring for 10 seconds. After the stirring, these nonwoven fabric were sufficiently washed with distilled water and then dried at 100° C. for 5 minutes. The weight gains of the resulting nonwoven fabrics were determined and the results are listed in the following Table 3.

TABLE 3

| Kind of Nonwoven Fabric | Zinc Oxide Concentration in Aqueous Suspension | |
|---|---|---|
| | 0.2% by weight | 0.5% by weight |
| Free of Surfactant Treatment | 2.6% by weight | 2.5% by weight |
| Treated with Surfactant | 3.0% by weight | 2.9% by weight |

In Example 5, the effect of the surfactant treatment was proved. The similar results could be obtained when using an acid, an alkali or an alcohol in place of a surfactant.

COMPARATIVE EXAMPLE 3

Titanium dioxide (3 g) was dispersed in one liter of de-ionized water and sufficiently stirred to give an aqueous suspension. The pH value of this suspension was found to be 7.5. A polypropylene nonwoven fabric (prepared by the spunbonding method; basis weight: 20 g/m$^2$; fiber diameter: about 20 μm; size: 10 cm×10 cm) was immersed in the aqueous suspension maintained at room temperature and stirred for 30 seconds. After the stirring, the nonwoven fabric was sufficiently washed with distilled water and then dried at 100° C. for 5 minutes.

The weight gain of the nonwoven fabric was found to be 2.3% by weight. Moreover, the nonwoven fabric thus treated was examined by the X-ray diffraction analysis and it was proved that the nonwoven fabric showed the diffraction peaks ascribed to titanium dioxide. Moreover, the fibrous surface of the nonwoven fabric was observed using a scanning electron microscope (SEM) and as a result, it was confirmed that the titanium dioxide particles were not adhered to the fibrous surface of the nonwoven fabric and simply caught in spaces between fibers.

When the titanium dioxide-carrying nonwoven fabric was stirred in de-ionized water for one hour, there were observed white fine particles in the de-ionized water. As a result of analysis, the white fine particles were proved to be titanium dioxide. In other words, titanium dioxide could not adhered to the substrate surface even if the method of the present invention was applied.

EXAMPLE 6

To one liter of de-ionized water, there was added 5 g of zinc oxide powder (primary particle size of about 0.2 μm) produced according to the dry method, followed by sufficient stirring to give a suspension. An aqueous sulfuric acid solution or an aqueous sodium hydroxide solution was added to the suspension to give suspensions each having a pH value listed in the following Table 4. A polypropylene nonwoven fabric (prepared by the spunbonding method; basis weight: 20 g/m$^2$; fiber diameter: about 20 μm; size: 10 cm×10 cm) was immersed in each suspension maintained at room temperature, followed by stirring for 30 seconds. After completion of the stirring, the nonwoven fabrics were sufficiently washed with distilled water and then dried at 100°

C. for 5 minutes. The relation between the pH value of the suspension and the weight gain of each nonwoven fabric was determined. The results obtained are summarized in the following Table 4:

TABLE 4

| pH of Suspension | Rate of Weight Gain of Nonwoven Fabric |
|---|---|
| 6.2 | 1.2% by weight |
| 7.6 | 3.5% by weight |
| 8.5 | 3.8% by weight |
| 9.5 | 2.7% by weight |
| 10.7 | 2.2% by weight |
| 12.2 | 2.0% by weight |

As seen from the data listed in Table 4, zinc oxide fine particles are particularly favorably adhered to a nonwoven fabric at a pH ranging from about 7 to 9, i.e., neutral to weak alkaline pH region.

EXAMPLE 7

A nonwoven fabric consisting essentially of polypropylene fibers was treated with a surfactant to thus make the surface hydrophilic. This surfactant-treated nonwoven fabric was immersed in aqueous zinc sulfate solution (2N) maintained at 90° C., followed by spraying the nonwoven fabric with an aqueous sodium hydroxide solution (2N) maintained at 90° C. immediately after removing it from the zinc sulfate solution, immersing it in an aqueous sodium sulfate solution (0.5N) immediately after the spraying, boiling at 100° C. for 20 minutes, then washing the nonwoven fabric with water and drying the fabric.

The nonwoven fabric thus treated was examined by the X-ray diffraction analysis and there were observed diffraction peaks to be ascribed to zinc oxide. In addition it was also observed by an electron microscope and it was confirmed that zinc oxide fine particles having a particle size of not more than 100 nm were approximately uniformly adhered to the fiber surface of the nonwoven fabric. The touch of the nonwoven fabric after the zinc oxide treatment was almost identical to that of the nonwoven fabric prior to the treatment and there was not observed any dropping or scattering of zinc oxide particles even when two such nonwoven fabrics were manually rubbed together.

Moreover, the zinc oxide-adhered nonwoven fabric (10cm×10cm) thus prepared was introduced into a sealable glass container (inner volume: 9.21), acetaldehyde gas was injected into the container to a concentration of 50 ppm and then the container was sealed. A black light (10W×5 lamps) was switched on and the contents of the container was irradiated with the light rays from the black light through the wall of the container. After the irradiation for 300 minutes, the acetaldehyde gas concentration in the glass container was determined and found to be not more than the detection limit (1 ppm). This clearly indicates that the zinc oxide-adhered nonwoven fabric exhibits a photocatalytic effect.

EXAMPLE 8

A cotton cloth was immersed in an aqueous zinc chloride solution (2N) maintained at 70° C. and then withdrawn from the solution, followed by immersing the cotton cloth in an aqueous sodium hydroxide solution (2N) maintained at 80° C. and then boiling it therein at 80° C. for 10 minutes. The pH value of the solution was 11 at this stage and a large amount of zinc oxide was deposited on and adhered to the cotton cloth. Thereafter the cotton cloth was washed with water and dried.

The zinc oxide-adhered cotton cloth thus obtained was placed in a laboratory dish and 150 µl each of a culture medium of *Escherichia coli* (including about 2×10$^4$ *E. coli* cells) was dropwise added to these laboratory dishes. The culture medium was recovered from the cotton cloths by washing them immediately after the dropwise addition and after 1, 2 and 3 hours from the dropwise addition, followed by cultivation thereof on a standard agar medium for 24 hours and counting the number of colonies. Separately, the same test was carried out using a cotton cloth free of zinc oxide by way of comparison. The results thus obtained are summarized in the following Table 5. The data listed in Table 5 reduced values.

TABLE 5

| Contact Time | Number of Colonies After Cultivation | |
|---|---|---|
| with Bacterial Culture Medium | Carrying Zinc Oxide Adhered | Free of Adhered Zinc Oxide |
| 0 hour | 2.1 × 10$^4$ | 2.1 × 10$^4$ |
| 1 hour | 5.6 × 10$^3$ | 1.9 × 10$^4$ |
| 2 hours | 4.5 × 10$^2$ | 1.9 × 10$^4$ |
| 3 hours | 5.2 × 10$^1$ | 2.0 × 10$^4$ |

The zinc oxide-adhered cotton cloth thus prepared was washed 40° C. according to the washing method as defined in JIS L0217 (1995) No. 103. The cotton cloth after the washing was observed by an electron microscope and it was confirmed that zinc oxide was adhered to the cotton cloth after washing like the cloth prior to washing.

When the cotton cloth was used as a filter, it was found to be an antibacterial filter of cotton woven fabric showing an effect almost identical to the foregoing data and thus *E. coli* cells adhered to the filter could be killed.

EXAMPLE 9

A zinc oxide-adhered filter was produced by treating a dust collecting and deodorizing filter for room air conditioner (a nonwoven fabric of synthetic fibers)(RB-A402D; available from Toshiba Corporation) in the same manner used in Example 7 to thus adhere zinc oxide to the filter. The zinc oxide-adhered filter and a filter free of zinc oxide each was fitted to a room air conditioner (RAS-251 LT; available from Toshiba Corporation) and the air conditioners were used in a standard home in the usual manner over 6 months.

After 6 months, any deposit on the front and rear faces of each filter were transferred to food stamps (standard agar medium available from Nissui Pharmaceutical Co., Ltd.) and cultivated in an incubator in order to inspect the filters for the standard plate count. As a result, there were observed colonies of bacteria on all of the 6 positions on the front and rear faces of the untreated filter, while bacterial colonies were observed only on one position out of 6 positions on the front and rear faces of the zinc oxide-adhered filter. This clearly indicates that the zinc oxide-adhered filter shows an antibacterial action.

EXAMPLE 10

A polypropylene film (thickness: 500 μm) was treated with a surfactant to thus make the surface thereof hydrophilic. The film thus treated was immersed in an aqueous zinc sulfate solution (2N) maintained at 90° C., followed by withdrawing from the solution, immersing it in an aqueous sodium hydroxide solution (2N) and adjusting the pH thereof to 11 by the addition of sulfuric acid. Thereafter the solution including the film was boiled at 100° C. for 15 minutes. A large amount of zinc oxide particles were deposited on and adhered to the film, followed by sufficient washing with water and drying at 70° C.

It was confirmed that zinc oxide fine particles having a particle size of not more than 100 nm were firmly and approximately uniformly adhered to the film surface. The film was examined by a visible-ultraviolet spectrophotometer and it was found that the zinc oxide-adhered film showed a UV absorbing effect, i.e., a transmittance to UV light of 200 nm of 9% while the transmittance of the film free of zinc oxide to UV light of 200 nm was found to be 92%.

EXAMPLE 11

A filter of glass fibers was treated with a surfactant to thus make the surface thereof hydrophilic. This surfactant-treated filter was immersed in aqueous zinc sulfate solution (1N) maintained at 90° C., followed by spraying the filter with an aqueous sodium hydroxide solution (1N) maintained at 90° C. immediately after removing it from the zinc sulfate solution, immersing it in an aqueous sodium sulfate solution (0.5N) immediately after the spraying, boiling at 100° C. for 10 minutes, then washing the filter with water and drying it.

The filter thus treated was examined by the X-ray diffraction analysis and there were observed diffraction peaks to be ascribed to zinc oxide. In addition it was also observed by an electron microscope and it was confirmed that zinc oxide fine particles having a particle size of not more than 100 nm were approximately uniformly adhered to the glass fiber surface of the filter. The zinc oxide-adhered filter is suitable for use as an air-cleaning filter.

EXAMPLE 12

A sheet of Japanese paper was immersed in aqueous zinc sulfate solution (1N) maintained at 70° C., followed by spraying the paper with an aqueous sodium hydroxide solution (2N) maintained at 60° C. immediately after removing it from the zinc sulfate solution, immersing it in an aqueous sodium sulfate solution (0.5N) immediately after the spraying, boiling at 60° C. for 5 minutes, then washing the paper with water and drying it.

The paper thus treated was observed by an electron microscope and it was confirmed that zinc oxide fine particles having a particle size of not more than 100 nm were approximately uniformly adhered to the pulp surface of the paper. The touch of the zinc oxide-adhered Japanese paper was almost identical to that observed for the paper prior to the treatment.

EXAMPLE 13

A nonwoven filter of glass fibers was immersed in aqueous zinc chloride solution (2N) maintained at 90° C., followed by spraying the nonwoven filter with an aqueous sodium hydroxide solution (2N) maintained at 90° C. immediately after removing it from the zinc chloride solution, then immersing it in an aqueous sodium chloride solution (0.5N), boiling at 100° C. for 20 minutes, then washing the nonwoven filter with water and drying it.

The filter thus treated was examined by the X-ray diffraction analysis and there were observed diffraction peaks to be ascribed to zinc oxide. In addition it was also observed by an electron microscope and it was confirmed that zinc oxide fine particles having a particle size of not more than 100 nm were approximately uniformly adhered to the glass fiber surface of the filter.

The zinc oxide-adhered filter was used as an air cleaning filter in combination with a ventilation fan and operated over one month. After one month, the filter was washed with sterilized distilled water, followed by smearing the washing water onto a standard agar culture medium and cultivation thereof at 37° C. for one day. However, any bacterial colony was not detected. In other words, it was confirmed that any bacterium was not proliferated on the zinc oxide-adhered filter.

EXAMPLE 14

A nonwoven fabric of polypropylene fibers was treated with a surfactant to thus make the surface thereof hydrophilic. The nonwoven fabric thus treated was immersed in an aqueous zinc sulfate solution (2N) maintained at 60° C., followed by immersing it in an aqueous sodium hydroxide solution (2N) immediately after withdrawing it from the solution. Thereafter the solution including the nonwoven fabric was boiled at 60° C. for 20 minutes, followed by washing the nonwoven fabric with water and drying.

The nonwoven fabric thus treated was examined by the X-ray =diffraction analysis and there were observed diffraction peaks to be ascribed to zinc oxide. In addition, it was also observed by an electron microscope and it was confirmed that zinc oxide fine particles having a particle size of not more than 100 nm were approximately uniformly adhered to the surface of the nonwoven fabric. The touch of the zinc oxide-adhered nonwoven fabric was almost identical to that of the nonwoven fabric prior to the treatment and there was not observed any dropping or scattering of zinc oxide particles even when two such nonwoven fabrics were manually rubbed together.

The nonwoven fabric (10 cm×10 cm) was placed in a sealable glass container (9.21 volume) and methyl mercaptan was injected into the container at a concentration of 40 ppm and the container was sealed. After 20 minutes, the concentration was reduced to not more than 1 ppm. This clearly indicates that the nonwoven fabric treated with zinc oxide shows a deodorizing activity.

The zinc oxide-adhered nonwoven fabric was used as a liner for paper diapers and it showed a practically acceptable sufficient deodorizing effect.

EXAMPLE 15

To the zinc oxide-adhered nonwoven fabric prepared in Example 14, there was dropwise added 150 μl of a culture medium of *Escherichia coli* (including about $2 \times 10^4$ *E. coli* cells). The culture medium was recovered from the surface of the zinc oxide-adhered nonwoven fabric immediately after the dropwise addition and after 1, 2 and 3 hours from the dropwise addition, followed by cultivation thereof on a standard agar medium for 24 hours and counting the number of colonies formed. Separately, the same test was carried out using a nonwoven fabric free of zinc oxide by way of comparison. The results thus obtained are summarized in the following Table 6. The data listed in Table 6 are reduced values.

TABLE 6

| Contact Time with Bacterial Culture Medium | Number of Colonies After Cultivation | |
|---|---|---|
| | Carrying Zinc Oxide Adhered | Free of Adhered Zinc Oxide |
| 0 hour | $2.3 \times 10^4$ | $2.3 \times 10^4$ |
| 1 hour | $4.8 \times 10^3$ | $2.0 \times 10^4$ |
| 2 hours | $2.2 \times 10^2$ | $2.1 \times 10^4$ |
| 3 hours | $1.9 \times 10^1$ | $1.9 \times 10^4$ |

Moreover, the zinc oxide-adhered nonwoven fabric thus prepared was washed at 40° C. according to the washing method as defined in JIS L0217 (1995) No. 103. The cloth after the washing was observed by an electron microscope and it was confirmed that zinc oxide was adhered to the cloth even after washing.

When the zinc oxide-adhered nonwoven fabric was applied to sanitary goods such as paper diapers, disposable towels and table napkins, they showed sufficient antibacterial activities and the nonwoven fabric could effectively control the proliferation of bacteria on the used sanitary goods.

EXAMPLE 16

A nonwoven fabric of polypropylene fibers was treated with a surfactant to thus make the surface thereof hydrophilic. The nonwoven fabric thus treated was immersed in an aqueous zinc sulfate solution (2N) maintained at 60° C., followed by pouring the aqueous zinc sulfate solution in which the nonwoven fabric was immersed in an equal volume of an aqueous sodium hydroxide solution (2N), maintaining the mixture at 60° C. for 20 minutes, washing the nonwoven fabric with water and drying the same.

The nonwoven fabric thus treated was examined by the X-ray diffraction analysis and there were observed diffraction peaks to be ascribed to zinc oxide. In addition, it was also observed by an electron microscope and it was confirmed that zinc oxide fine particles having a particle size of not more than 100 nm were approximately uniformly adhered to the surface of the nonwoven fabric. The touch of the zinc oxide-adhered nonwoven fabric was almost identical to that of the nonwoven fabric prior to the treatment and there was not observed any dropping or scattering of zinc oxide particles even when two such nonwoven fabrics were manually rubbed together.

To the zinc oxide-adhered nonwoven fabric, there was dropwise added 150 $\mu$l of a culture medium of Methicillin-resistant *Staphylococcus aureus* (MRSA) (including about $2\times10^4$ MRSA cells). The culture medium was recovered from the surface of the zinc oxide-adhered nonwoven fabric immediately after the dropwise addition and after 1, 2 and 3 hours from the dropwise addition, followed by cultivation thereof on a standard agar medium for 24 hours and counting the number of colonies formed. Separately, the same test was carried out using a nonwoven fabric free of zinc oxide by way of comparison. The results thus obtained are summarized in the following Table 7. The data listed in Table 7 are reduced values.

TABLE 7

| Contact Time with Bacterial Culture Medium | Number of Colonies After Cultivation | |
|---|---|---|
| | Carrying Zinc Oxide Adhered | Free of Adhered Zinc Oxide |
| 0 hour | $2.0 \times 10^4$ | $2.0 \times 10^4$ |
| 1 hour | $1.3 \times 10^3$ | $1.6 \times 10^4$ |
| 2 hours | $3.6 \times 10^2$ | $8.8 \times 10^3$ |
| 3 hours | $7.2 \times 10^1$ | $1.1 \times 10^4$ |

Moreover, the zinc oxide-adhered nonwoven fabric thus prepared was washed at 40° C. according to the washing method as defined in JIS L0217 (1995) No. 103. The nonwoven fabric after the washing was observed by an electron microscope and it was confirmed that zinc oxide was adhered to the nonwoven fabric even after washing.

An antifungal activity test was carried out using the zinc oxide-adhered nonwoven fabric according to the method specified in JIS-Z2911. Moreover, the same test was also carried out using the same nonwoven fabric free of zinc oxide by way of comparison. After 28 days, the growth conditions of mold hyphae were observed. As a result, there was observed the growth of mold hyphae on almost the whole surface of the nonwoven fabric free of zinc oxide (antifungal index "1"), but the growth of the mold hypha was not observed at all on the zinc oxide-adhered nonwoven fabric (antifungal index "3").

The foregoing results indicate that the zinc oxide-adhered nonwoven fabric has satisfactory antibacterial and antifungal activities. Thus the nonwoven fabric can accordingly be used as an antibacterial sheet, an antifungal sheet and has an effect of controlling the proliferation of ticks which utilize mold as nutrients. When the zinc oxide-adhered nonwoven fabric was put between a carpet and tatami mat as an underlay, the nonwoven fabric showed sufficient antibacterial and antifungal activities and could accordingly control the proliferation of bacteria and/or development of mold on the used underlay.

EXAMPLE 17

Nonwoven fabrics (10 cm×10 cm) consisting essentially of polypropylene fibers each was treated with a surfactant to thus convert the surface thereof into hydrophilic one. Each surfactant-treated nonwoven fabric was immersed in an aqueous zinc sulfate solution (2N) maintained at a temperature specified in the following Table 8, followed by immersing it in an aqueous sodium hydroxide solution maintained at the same temperature for 30 minutes immediately after removing it from the zinc sulfate solution. At this stage, the pH value of the sodium hydroxide solution after the immersion of the fabric was adjusted to the level specified in Table 8. Thereafter each nonwoven fabric was sufficiently washed with water and dried at the same temperature (provided that the nonwoven fabric was air-dried when the reaction temperature was less than 500° C.).

Each nonwoven fabric thus treated was examined by the X-ray diffraction analysis to thus determine the chemical species of the particles adhered and the rate of weight gain of each nonwoven fabric was also determined. The results thus obtained are summarized in the following Table 8 along with the temperature and pH values at which the results were determined.

TABLE 8

| Temp. | | pH Value | | | |
|---|---|---|---|---|---|
| ° C. | | 5.5 | 8.1 | 10.4 | 14.2 |
| 92 | chemical species | X | ○ | ○ | ○ |
| | rate of weight gain | — | 2.8% | 3.9% | 4.3% |
| 75 | chemical species | X | ○ | ○ | ○ |
| | rate of weight gain | — | 2.5% | 3.1% | 3.9% |
| 50 | chemical species | X | ○ | ○ | ○ |
| | rate of weight gain | — | 1.6% | 3.3% | 3.1% |
| 24 | chemical species | X | ○ | ○ | ○ |
| | rate of weight gain | — | 1.9% | 2.3% | 2.0% |
| 8 | chemical species | X | ○ + X | ○ + X | Δ |
| | rate of weight gain | — | 3.4% | 3.9% | — |

In the above table 8, ○ represents zinc oxide (ZnO), × represents basic zinc sulfate ($6Zn(OH)_2 \cdot 4H_2O$) and Δ represents zinc hydroxide ($Zn(OH)_2$). The mixtures obtained under condition of 8° C. and pH 8.1 or pH 10.4 contained minor amount of zinc oxide and major amount of basic zinc sulfate in molar ratio judging from X-ray diffraction analysis. Therefore, the amount of zinc oxide in the mixture was less than 9% by weight molecular weight of zinc oxide)/ [(molecular weight of basic zinc (molecular weight of zinc oxide)].

As seen from the data listed in Table 8, zinc oxide fine are firmly bonded to the surface of a substrate without using any binder when reacting at a temperature of not less than room temperature and under alkaline conditions. The amount of zinc oxide particles adhered to the substrate surface has a tendency to increase as the reaction temperature is raised. In addition, there was not observed any release of the deposit in any case.

We claim:

1. A zinc oxide fine particle-adhered composite material showing antibacterial, deodorizing, UV absorbing, photocatalytic, stain-proofing and purifying activities, which consists essentially of a substrate selected from the group consisting of fibers, fibrous substrates, paper products, molded articles of synthetic resins, films and ceramics and zinc oxide fine particles having an average particle size of not more than 0.5 μm adhered thereto, wherein the zinc oxide fine particles deposited, from an aqueous medium, on the surface of the substrate are firmly adhered to the surface without using any binder and the zinc oxide fine particles are substantially exposed on the surface of the substrate.

2. The zinc oxide fine particle-adhered composite material as set forth in claim 1 wherein the zinc oxide fine particles are those deposited on the surface of the substrate from an aqueous suspension of zinc oxide fine particles.

3. The zinc oxide fine particle-adhered composite material of claim 1 wherein the zinc oxide fine particles are those deposited on the surface of the substrate by coming the substrate carrying a zinc ion-containing acidic solution attached thereto in contact with an aqueous alkaline solution to thus cause a reaction therebetween under alkaline conditions and having an average particle size of not more than 0.1 μm.

4. The zinc oxide fine particle-adhered composite material of claim 1 wherein the substrate is a fiber, a fibrous product or a paper product.

5. The zinc oxide fine particle-adhered composite material of claim 4 wherein the substrate is a thermoplastic fiber or a thermoplastic fiber product.

6. The zinc oxide fine particle-adhered composite material of claim 4 wherein the substrate is woven or nonwoven fabric.

7. The zinc oxide fine particle-adhered composite material of claim 1 wherein it is an antibacterial filter having gas permeability and water permeability.

8. The zinc oxide fine particle-adhered composite material of claim 1 wherein it is an antibacterial, deodorizing sanitary good.

9. The zinc oxide fine particle-adhered composite material of claim 1 wherein it is an antibacterial, antifungal fibrous sheet.

10. A method for preparing a zinc oxide fine particle-adhered composite material which shows antibacterial, deodorizing, UV absorbing, photocatalytic, stain-proofing and purifying activities, which consists essentially of a substrate selected from the group consisting of fibers, fibrous substrates, paper products, molded articles of synthetic resins, films and ceramics and zinc oxide fine particles adhered thereto, in which the zinc oxide fine particles having an average particle size of not more than 0.5 μm are firmly adhered to the surface without using any binder and the zinc oxide fine particles are substantially exposed on the surface of the substrate, wherein the method comprises the step of contacting an aqueous suspension of zinc oxide fine particles with the substrate to thus deposit the zinc oxide fine particles on the surface of the substrate.

11. The method as set forth in claim 10 wherein the concentration of the zinc oxide fine particles in the aqueous suspension is not more than 1% by weight.

12. The method as set forth in claim 10 wherein the substrate is pre-treated with a surfactant, an acid, an alkali, an alcohol, ozone, ultraviolet rays or radiant rays, prior to use.

13. The method as set forth in claim 10 wherein the substrate is brought into contact with the aqueous suspension of zinc oxide fine particles by immersing the substrate in the aqueous suspension, spraying the substrate with the aqueous suspension or coating the substrate with the aqueous suspension.

14. The method as set forth in claim 10 wherein the substrate is a fiber, a fibrous product or a paper product.

15. A method for preparing a zinc oxide fine particle-adhered composite material which shows antibacterial, deodorizing, UV absorbing, photocatalytic, stain-proofing and purifying activities, which consists essentially of a substrate selected from the group consisting of fibers, fibrous substrates, paper products, molded articles of synthetic resins, films and ceramics and zinc oxide fine particles adhered thereto, in which the zinc oxide fine particles having an average particle size of not more than 0.1 μm are firmly adhered to the surface without using any binder and the zinc oxide fine particles are substantially exposed on the surface, wherein the method comprises the step of contacting the substrate carrying a zinc ion-containing acidic solution attached thereto with an aqueous alkaline solution to thus cause a reaction therebetween under alkaline conditions.

16. The method of claim 15 wherein the substrate carrying the zinc ion-containing acidic solution attached thereto is brought into contact with the aqueous alkaline solution at a temperature of not less than 50° C. to thus cause the reaction under alkaline conditions.

17. The method as set forth in claim 15 wherein the substrate is a fiber, a fibrous product or a paper product.

18. A method for preparing a zinc oxide fine particle-adhered composite material which shows antibacterial, deodorizing, UV absorbing, photocatalytic, stain-proofing and purifying activities, which consists essentially of a substrate selected from the group consisting of fibers, fibrous substrates, paper products, molded articles of synthetic resins, films and ceramics and zinc oxide fine particles adhered thereto, in which the zinc oxide fine particles having an average particle size of not more than 0.1 μm are firmly adhered to the surface without using any binder and the zinc oxide fine particles are substantially exposed on the surface, wherein the method comprises the steps of contacting the substrate carrying a zinc ion-containing acidic solution attached thereto with an aqueous alkaline solution to thus cause a reaction therebetween under alkaline conditions and, immediately thereafter, ripening in a solution which hardly solubilizes zinc oxide for a time of not less than 5 minutes.

19. The method of claim 18 wherein the substrate carrying the zinc ion-containing acidic solution attached thereto is brought into contact with the aqueous alkaline solution at a temperature of not less than 50° C. to thus cause the reaction under alkaline conditions and, immediately thereafter, ripening in the solution which hardly solubilizes zinc oxide at a temperature of not less than 50° C. for a time of not less than 5 minutes.

20. The method as set forth in claim 18 wherein the substrate is a fiber, a fibrous product or a paper product.

* * * * *